United States Patent [19]

Pera et al.

[11] Patent Number: 5,356,548
[45] Date of Patent: Oct. 18, 1994

[54] 1-METHYL-3,5,7-TRIAZA-1-AZONIATRICYCLODECANE COMPOUNDS, A METHOD FOR PREPARING THESE COMPOUNDS, THEIR USE IN THE CONTROL OF MICROORGANISMS IN AQUEOUS SYSTEMS, AND THEIR USE IN THE INHIBITION OF CORROSION

[75] Inventors: John D. Pera, Cordova; S. Rao Rayudu, Germantown, both of Tenn.

[73] Assignee: Buckman Laboratories International, Inc., Memphis, Tenn.

[21] Appl. No.: 53,407

[22] Filed: Apr. 28, 1993

Related U.S. Application Data

[62] Division of Ser. No. 732,759, Jul. 19, 1991, Pat. No. 5,245,031, which is a division of Ser. No. 174,819, Mar. 29, 1988, Pat. No. 5,061,797.

[51] Int. Cl.$^5$ .............. C10M 137/00; C10M 139/00; C09D 5/14
[52] U.S. Cl. .................. 252/49.3; 252/49.5; 252/11; 523/122; 106/18.3; 106/18.32; 422/12; 422/13; 422/15; 422/16; 422/18; 422/19; 514/244
[58] Field of Search ............ 252/49.3, 49.5, 400.2, 252/400.21, 400.4, 400.54, 401, 34, 11; 523/122; 106/18.32, 18.3; 422/1, 7, 12, 13, 15, 16, 19, 14, 18; 514/244

[56] References Cited

U.S. PATENT DOCUMENTS

| | | |
|---|---|---|
| 1,336,709 | 4/1920 | Tschunke . |
| 4,505,831 | 3/1985 | Fenyes et al. . |
| 4,650,866 | 3/1987 | Rayudu . |
| 4,671,934 | 6/1987 | Terry et al. . |
| 4,892,583 | 1/1990 | Rayudu . |
| 4,920,107 | 4/1990 | Pera et al. ............ 514/244 |
| 5,023,332 | 6/1991 | Rayudu . |
| 5,061,797 | 10/1991 | Pera et al. . |

OTHER PUBLICATIONS

Friedrich et al., Zur Kenntnis des Hexamethylentetramins I., 54B Berichte 1531–42 (1921). (Month Unknown).

Primary Examiner—Prince Willis, Jr.
Assistant Examiner—Alan D. Diamond
Attorney, Agent, or Firm—Finnegan, Henderson, Farabow, Garrett & Dunner

[57] ABSTRACT

Compounds of the formula

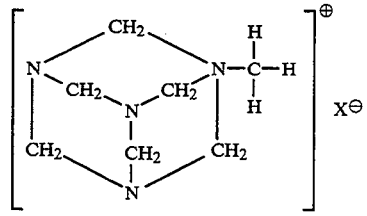

wherein X is an anion selected from the group consisting of phosphate, borate and molybdate groups, and a method for making these compounds. The compounds are useful in the control of microorganisms in aqueous systems and in the inhibition of corrosion of metal surfaces in contact with aqueous systems.

13 Claims, No Drawings

1-METHYL-3,5,7-TRIAZA-1-AZONIATRICYCLO-DECANE COMPOUNDS, A METHOD FOR PREPARING THESE COMPOUNDS, THEIR USE IN THE CONTROL OF MICROORGANISMS IN AQUEOUS SYSTEMS, AND THEIR USE IN THE INHIBITION OF CORROSION

This is a division of application Ser. No. 07/732,759, filed Jul. 19, 1991, now U.S. Pat. No. 5,245,031, which is a division of application Ser. No. 07/174,819, filed Mar. 29, 1988 now U.S. Pat. No. 5,061,797.

FIELD OF THE INVENTION

The present invention relates to a method for the preservation of aqueous systems which are susceptible to microbiological degradation through the use of certain 1-methyl-3,5,7-triaza-1-azoniatricyclodecane compounds. Typical systems include aqueous solutions, emulsions and suspensions.

The present invention also relates to the novel compounds 1-methyl-3,5,7-triaza-1-azoniatricyclodecane phosphate, 1-methyl-3,5,7-triaza-1-azoniatricyclodecane borate and 1-methyl-3,5,7-triaza-1-azoniatricyclodecane molybdate, and a method for their preparation.

The present invention further relates to a method for inhibiting the corrosion of metal surfaces, preferably iron and iron alloys and more preferably low carbon steel, in contact with an aqueous system, by employing the 1-methyl-3,5,7-triaza-1-azoniatricyclodecane compounds of the invention.

BACKGROUND OF THE INVENTION

A large number of commercial and industrial products comprise aqueous systems containing organic materials. Examples are latexes, surfactants, dispersants, stabilizers, thickeners, adhesives, starches, waxes, proteins, emulsifying agents, detergents, cellulose products, and resins formulated in aqueous solutions, emulsions or suspensions. Such products frequently contain relatively large amounts of water. The temperature at which these products are stored, as well as their pH, makes these products susceptible to the growth of microorganisms. These microorganisms can be introduced during the manufacturing of these products (from exposure to air, tanks, pipes, equipment, and humans), and/or during their use (from multiple openings and reclosures of packaged products, and introduction of contaminated objects to stir or remove material).

Microbiological degradation of aqueous systems containing organic material may manifest itself in a variety of problems. These include loss of viscosity, gas formation, objectionable odors, decreased pH, emulsion breaking, color change, and gelling.

Additionally, aqueous systems, such as cooling water and related water-handling systems, which include cooling towers and associated pumps, heat exchangers, and pipelines, heating systems, gas scrubbing systems and other similar systems commonly encounter problems of corrosion, including the electrochemical corrosion of iron and iron alloys in contact with the circulating water.

For many years, the most common method of controlling corrosion in cooling water and related water-handling systems was to treat the water with hexavalent chromium salts, such as sodium chromate. At the same time, scaling due to slightly soluble calcium salts was prevented by treating the water with mineral acids, such as sulfuric acid, to keep the pH low enough to prevent the precipitation of the scale forming calcium salts. Improvements in this technology over the years included the use of zinc salts and phosphates in combination with the chromates, which could provide good corrosion control at reduced chromate concentrations. However, because of environmental concerns over the discharge of even small amounts of hexavalent chromium in cooling water effluents, new methods continued to be sought that would provide total corrosion inhibition without the use of hexavalent chromium.

Some of the ways that this has been achieved include the use of various combinations of zinc salts, phosphates, polyphosphates, and organic phosphoric acid derivatives and their salts. However, all of these methods in the prior art have certain disadvantages, such as requiring close control of the pH to keep it within a very narrow range or using special additives or dispersants to prevent the precipitation of scale-forming salts like calcium phosphate.

Friedrich et al., *Zur Kenntnis des Hexamethylentetramins. I.*, 54B Berichte 1531-42 (1921), discloses 1-methyl-3,5,7-triaza-1-azoniatricyclodecane compounds which include anions such as methyl sulfate, nitrate, picrate, perchlorate, and thiocyanate groups.

U.S. Pat. Nos. 4,505,831 and 4,650,866 disclose 1-methyl-3,5,7-triaza-1-azoniatricyclodecane compounds, useful as microbicides. These patents, however, are limited to such compounds having halide anions, which are not corrosion inhibiting compounds. U.S. Pat. No. 4,650,866 also discloses a method for preparing such 1-methyl-3,5,7-triaza-1-azoniatricyclodecane halides comprising the reaction of an ammonium halide with methylamine, formaldehyde and ammonia in an aqueous medium.

DESCRIPTION OF THE INVENTION

The present invention provides a method for the preservation of an aqueous system which is susceptible to microbiological degradation, comprising the step of adding to the system a compound having the formula

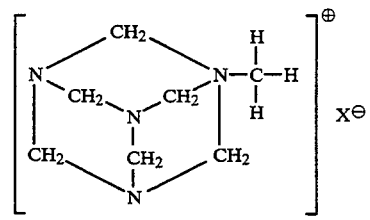

wherein X is an anion selected from the group consisting of phosphate, borate and molybdate groups, and wherein the compound is added in an amount sufficient to inhibit the growth and proliferation of at least one microorganism in the aqueous system.

The compounds of the invention inhibit the corrosion of metals, such as iron, and may advantageously be employed in the preservation of aqueous systems held in metal containers.

A preferred method for preparing the compounds of the invention comprises the reaction of a starting compound selected from the group consisting of ammonium phosphate, ammonium molybdate and hydroboric acid, with methylamine, formaldehyde and ammonia in an aqueous medium. Ammonium phosphate may be used in this process as the starting compound in the preparation of 1-methyl-3,5,7-triaza-1-azoniatricyclodecane phosphate, ammonium molybdate may be used as the starting compound in the preparation of 1-methyl-3,5,7-triaza-1-azoniatricyclodecane molybdate, and hydroboric acid may be used as the starting compound in the preparation of 1-methyl-3,5,7-triaza-1-azoniatricyclodecane borate. This process is an economical method for making the compounds of the instant invention. All of the starting materials for this process are readily available commercial products.

In this method of preparation, each mole of starting compound is preferably reacted with about 0.75 to 2 moles of methylamine as a source of an N-methyl group, 5.75 to 2 moles of formaldehyde, and 1.75, more preferably 2, or more moles, of ammonia. Most preferably, from 2 to 4 moles of ammonia per mole of starting compound are used in this reaction.

The process of preparation is preferably conducted at a temperature of from about 40° to 70° C. More preferably, the process is conducted in the range of about 45° to 50° C.

The reaction is conducted for a time sufficient to prepare the quaternary ammonium salts of the present invention. Preferably, the reaction is conducted for about 2 hours to 6 hours, more preferably for about 2 hours.

The method of this invention may be used to prevent microbiological degradation in any aqueous system susceptible to such degradation, such as aqueous solutions, emulsions and suspensions.

Examples of aqueous solutions, emulsions, and suspensions which are subject to microbiological degradation include water-based paints, latex emulsions, such as acrylic and polyvinyl acetate emulsions, adhesive solutions and emulsions, wax emulsions, polishes, metalworking fluid solutions and emulsions, caulking and sealant products, papermaking chemical products such as alum solutions, clay and pigment dispersions, starch slurries and solutions, and protein coating formulations, and cosmetic preparations. Many of these materials are also used in other industrial and commercial products. Aqueous systems may be used in petroleum production and in the manufacture of detergents, surfactants, inks and textiles.

A particularly preferred use of the compounds of the present invention is in the preservation of water-based paints or cutting fluids, such as cutting oil solutions or emulsions.

The antimicrobial activity of the compounds used in accordance with the invention extends to a variety of different microorganisms, including bacteria such as *Escherichia coli*, *Staphylococcus aureus*, *Pseudomonas aeruginosa*, *Enterobacter aerogenes*, *Klebsiella pneumoniae*, *Proteus vulgaris*, *Salmonella choleraesuis* and *Bacillus subtilis*, and fungi such as *Candida albicans* and *Aspergillus niger*.

The concentration of the compounds of this invention which inhibits growth and proliferation of a microorganism, and thus provides the preservative effect described herein, may be readily determined by one skilled in the art without extensive experimentation and, preferably, will range from about 25 parts to about 5000 parts by weight of the compound for one million parts of the aqueous system to be preserved.

This invention also relate to a method for inhibiting corrosion of a metal surface in contact with an aqueous system comprising the step of treating the aqueous system with a compound of the formula

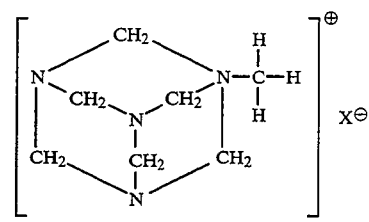

wherein X is an anion selected from the group consisting of phosphate, borate and molybdate groups, in an amount sufficient to inhibit corrosion of a metal surface exposed to an aqueous system.

The concentration of the compounds of this invention which inhibits corrosion may readily be determined by one skilled in the art without extensive experimentation.

This invention further relates to the novel compounds 1-methyl-3,5,7-triaza-1-azoniatricyclodecane phosphate, 1-methyl-3,5,7-triaza-1-azoniatricyclodecane borate, and 1-methyl-3,5,7-triaza-1-azoniatricyclodecane molybdate.

The compounds of the invention may be utilized as solids or may be dissolved in water prior to addition to the product being preserved. In those instances wherein the presence of water might cause some degradation of the quaternary ammonium salt over a long period of time, non-aqueous dispersions could be prepared by the proper selection of solvents, dispersants, and stabilizers which are well-known in the art as being suitable for the formation of such dispersions.

In those instances wherein the compounds of the invention are subject to rapid degradation by heat, stabilizers may be added.

To illustrate the nature of the invention, the following examples are given. It should be understood, however, that the invention is not to be limited to the specific conditions or details set forth in these examples.

EXAMPLE 1

Preparation of
1-Methyl-3,5,7-triaza-1-azoniatricyclodecane phosphate

A 250 ml, three-neck round-bottom flask equipped with a reflux condenser, a mechanical stirrer, a thermometer and a dropping funnel was charged with 28.6 g (0.25 mole) of ammonium phosphate and 15.6 g (0.25 moles) of 50% aqueous methylamine. To the above well-agitated mixture were slowly added 121.6 g (1.5 moles) of 37% aqueous formaldehyde, while maintaining the temperature between 45° C. and 50° C. After completing the addition and while continuing vigorous agitation, 30.4 g (0.50 mole) of 29% aqueous ammonia were introduced at such a rate as to maintain the temperature between 45° C. and 50° C. Stirring was continued for an additional 2 hours, while the temperature fell gradually to the ambient. The resulting water-clear solution was analyzed by HPLC. The solution contained 24.9% (72% yield) by weight of the 1-methyl-3,5,7-triaza-1-azoniatricyclodecane phosphate.

EXAMPLE 2

Preparation of 1-methyl-3,5,7-triaza-1-azoniatricyclodecane borate

A 500 ml, three-neck round-bottom flask equipped with a reflux condenser, a mechanical stirrer, a thermometer and a dropping funnel was charged with 29.3 g (0.50 mole) of 29% aqueous ammonia. To the above were slowly added 30.9 g (0.50 mole) of hydroboric acid, and 31.0 g (0.50 mole) of 50% aqueous methylamine. To the above well-agitated mixture were slowly added 243.3 g (3.0 moles) of 37% aqueous formaldehyde, while maintaining the temperature between 45° and 50° C. After completing this addition, and while continuing vigorous agitation, 58.6 g (1.0 mole) of 29% aqueous ammonia were introduced at such a rate as to maintain the temperature between 45° and 50° C. Stirring was continued for an additional 2 hours while the temperature fell gradually to the ambient. The resulting water-clear solution was analyzed by HPLC. The solution contained 29.1% (70% yield) by weight of 1-methyl-3,5,7-triaza-1-azoniatricyclodecane borate.

EXAMPLE 3

The preservative effectiveness of the quaternary ammonium salts prepared in Examples 1 and 2 was determined in a freshly prepared water-based paint formulated with titanium dioxide and calcium carbonate as pigments, an acrylic emulsion resin, dispersants, and hydroxyethyl cellulose as thickener. The pH of this paint was approximately 9.0. The procedure used was as follows:

A. Weigh 100 g. of paint into prenumbered French square bottles.

B. Add the appropriate amount of the preservative to obtain the desired parts per million.

C. Add 1 ml. of inoculum. Mix well by shaking the contents of each bottle immediately after the addition of the inoculum. The inoculum was prepared by adding 2 ml. of sterile saline solution to an 18- to 24-hr. agar culture of *Enterobacter aerogenes*, agitating to loosen the surface growth, and decanting to a sterile test tube. The procedure was repeated with cultures of *Pseudomonas aeruginosa* and *Bacillus subtilis*, and all three suspensions were decanted to the same test tube. The concentration of the mixed bacterial suspension was then adjusted so that a final concentration of $1 \times 10^5$ cells per ml. is achieved when one ml. of the inoculum is added to 100 ml. of the paint.

D. Include a minimum of two controls (bottles containing substrate and inoculum only).

E. Incubate at 37° C. for 9 weeks.

F. Streak from the contents of each bottle onto nutrient agar plates at intervals of 1 day, 2 days, 3 days, 7 days, and 21 days after each challenge. Incubate the streaked plates at 37° C. for 24 hours.

G. Reinoculate the test with the same test organisms at the end of 21 days and again at the end of 42 days.

H. Observe the streaked plates for growth after 24 hours of incubation.

I. Observe the contents of each bottle for 1. Color change 2. Odor 3. Thickening of paint J. Evaluate the results. A chemical is considered an effective preservative when it prevents the growth of bacteria 21 days after each inoculation.

The quaternary ammonium compounds described in Examples 1 and 2 were effective preservatives at concentrations of 200 parts of the salt per one million parts of paint and higher concentrations. No color changes were noted in any of the tests. In addition, no undesirable odors were observed and the viscosities of the preserved paint samples did not change.

EXAMPLE 4

The antimicrobial effectiveness of 1-methyl-3,5,7-triaza-1-azoniatricyclodecane borate was determined by the method for the preservation of an organic substance described in the United States Pharmacopeia, 21st revision (Jan. 1, 1985), "Microbiological Test #51" p. 1151. Test results are given in Table 1.

TABLE I

| COMPOUND | MINIMUM INHIBITORY CONCENTRATION (ppm) vs. | | | | |
|---|---|---|---|---|---|
| | E. coli | S. aureus | P. aeruginosa | C. albicans | A. niger |
| 1-methyl-3,5,7-triaza-1-azoniatricyclodecane borate | 300 | 300 | 100 | 500 | 200 |

EXAMPLE 5

The compounds of the present invention are also effective in preserving synthetic, soluble, and semi-synthetic metalworking fluids. The tests were conducted following ASTM's Evaluation of Antimicrobial Agents in Aqueous Metalworking Fluids (designation E686-80).

The quaternary ammonium compounds described in Examples 1 and 2 preserve the soluble-oil metalworking fluids against bacterial attack at 300 parts, the semi-synthetic oils at 200 parts, and the synthetic oils at 200 parts of these compounds per one million parts of the metalworking fluids.

EXAMPLE 6

Two compounds of the present invention were found to be especially effective as corrosion inhibitors. In a standard corrosion test, they were found to be corrosion inhibitors whereas 1-methyl-3,5,7-triaza-1-azoniatricyclodecane chloride (disclosed in U.S. Pat. No. 4,505,831) is not a corrosion inhibitor.

The test involves exposing cast iron chips obtained from Met Cut Research Associates of Cincinnati, Ohio, to the test material. 2.0 grams of chips are placed on 90 mm filter paper in the inverted cover of a petri dish. The chips are arranged in a one inch square by means of a plastic template. The chips are covered and the filter paper saturated with 25 ml of test solution.

After 18 hours at room temperature, the test solution and chips are removed. The level of corrosion is determined by observation of the staining by corrosion products in the one inch square. No staining is rated as 0. Complete coverage is rated 10. Values between 0 and 10 are assigned based on the area covered with stain.

The compounds were tested at 10 percent by weight aqueous dilutions. The results are given in Table II.

TABLE II

| Compound | Corrosion Rating |
|---|---|
| Control (Memphis Tap Water) | 10 |
| 1-Methyl-3,5,7-triaza-1-azoniatricyclodecane chloride | 10 |
| 1-Methyl-3,5,7-triaza-1-azoniatricyclodecane borate | 0 |
| 1-Methyl-3,5,7-triaza-1- | 0 |

TABLE II-continued

| Compound | Corrosion Rating |
|---|---|
| azoniatricyclodecane phosphate | |

We claim:

1. A method of preserving an aqueous system which is susceptible to microbiological degradation, comprising the step of adding to said system a compound having the formula

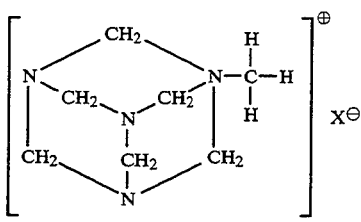

wherein X is an anion selected from the group consisting of phosphate, borate and molybdate groups, and wherein said compound is added in an amount sufficient to inhibit the growth and proliferation of at least one microorganism in said aqueous system.

2. The method of claim 1, wherein said aqueous system is selected from the group consisting of aqueous solutions, emulsions and suspensions.

3. The method of claim 2, wherein said aqueous system is a water-based paint.

4. The method of claim 2, wherein said aqueous system is a cutting fluid.

5. The method of claim 1, wherein said compound is 1-methyl-3,5,7-triaza-1-azoniatricyclodecane phosphate.

6. The method of claim 5, wherein said aqueous system is a water-based paint.

7. The method of claim 5, wherein said aqueous system is a cutting fluid.

8. The method of claim 1, wherein said compound is 1-methyl-3,5,7-triaza-1-azoniatricyclodecane borate.

9. The method of claim 8, wherein said aqueous system is a water-based paint.

10. The method of claim 8, wherein said aqueous system is a cutting fluid.

11. The method of claim 1, wherein said compound is 1-methyl-3,5,7-triaza-1-azoniatricyclodecane molybdate.

12. The method of claim 11, wherein said aqueous system is a water-based paint.

13. The method of claim 11, wherein said aqueous system is a cutting fluid.

* * * * *